United States Patent [19]
Ito et al.

[11] Patent Number: 5,069,676
[45] Date of Patent: Dec. 3, 1991

[54] SANITARY ARTICLE

[75] Inventors: Osamu Ito, Utsunomiya; Hiroshi Mizutani, Yachiyo, both of Japan

[73] Assignee: Kao Corporation, Tokyo, Japan

[21] Appl. No.: 83,918

[22] Filed: Aug. 7, 1987

Related U.S. Application Data

[63] Continuation of Ser. No. 714,153, Mar. 20, 1985, abandoned.

[30] Foreign Application Priority Data

Apr. 4, 1984 [JP] Japan ................................. 59-67023

[51] Int. Cl.$^5$ ............................................. A61F 13/15
[52] U.S. Cl. .................................... 604/358; 604/368; 604/378; 604/380
[58] Field of Search ................. 604/358, 368, 378–380

[56] References Cited

U.S. PATENT DOCUMENTS

| | | | |
|---|---|---|---|
| 3,375,827 | 4/1968 | Bletzinger et al. | 604/380 |
| 3,612,055 | 10/1971 | Mesek et al. | 604/378 |
| 4,251,643 | 2/1981 | Harada et al. | 604/368 |
| 4,269,188 | 5/1981 | Nishizawa et al. | 604/375 |
| 4,297,410 | 10/1981 | Tsuchiya | 604/366 |
| 4,333,462 | 6/1982 | Holtman et al. | 604/368 |
| 4,389,211 | 6/1983 | Lenaghan . | |
| 4,592,751 | 6/1986 | Gegelys | 604/380 |

FOREIGN PATENT DOCUMENTS

| | | |
|---|---|---|
| WO80/01455 | 7/1980 | PCT Int'l Appl. . |
| 547524 | 6/1979 | United Kingdom ................. 128/287 |
| 2017505 | 10/1979 | United Kingdom . |
| 2089214 | 6/1982 | United Kingdom . |

OTHER PUBLICATIONS

Translation of text of PCT WO80/01455.

Primary Examiner—John D. Yasko
Assistant Examiner—Anthony Gutowski
Attorney, Agent, or Firm—Flynn, Thiel, Boutell & Tanis

[57] ABSTRACT

In a sanitary article having as a core material a super water absorbing polymer and two layers of fluff pulp to envelop the polymer, the improvement comprises that said layer of fluff pulp is composed of a compressed first site and a further compressed second site, the density of said first site ranging from 0.04 to 0.15 g/cm$^3$, the density of said second site ranging from 0.06 to 0.4 g/cm$^3$, and the area of said second site ranging from 10 to 50% of that of the entire article.

7 Claims, 1 Drawing Sheet

SANITARY ARTICLE

This application is a continuation of U.S. Ser. No. 714,153, filed Mar. 20, 1985, now abandoned.

The invention relates to a sanitary article such as a disposable diaper which comprises a super water absorbing polymer as the absorbent core and two layers of fluff pulp to contain the polymer therebetween. In particular, the invention provides an improvement in the structure of the fluff pulp layer s that the absorbent polymer may serve as the main absorbent in comparison the fluff pulp layer.

The super water absorbing polymer is called also as a high-molecular water-absorptive material and the fluff pulp is called as cotton-like pulp.

Fluff pulp is used as absorptive core material in most of the commercially available disposable diapers at present. Although super water absorbing polymers have recently been used in some of them to supplement the fluff pulp, there are substantially no diapers in which super water absorbing polymers are used as principal absorber in the core material. The general requirements for the absorptive core material are to have large absorption capacity for the prevention of the leakage of urine from the diaper, to make the return of the absorbed urine to the surface as small as possible, and so on. It is a usual practice to increase the extent of compressing the pulp in order to rapidly diffuse the absorbed liquid to a wide area and reduce the wetness to the touch, so that the above-described requirements can be fulfilled better. However, the more highly the absorptive material is compressed, the more effectively it absorbs but at the same time the harder the material becomes. The compression of the absorptive material to maximize its effect has therefore not been effected practically.

Under these circumstances, the inventors have accomplished the present invention as the result of intensive studies to overcome this disadvantage, based on the finding which will be described in detail in the following paragraphs that the use of a combination of fluff pulp and a super water absorbing polymer which can absorb urine in an amount at least several tens of times as much as its own weight and moreover never releases the absorbed liquid, with partly varied degrees of compaction, brings about not only greater absorption capacity and smaller return of urine but also better touch of the absorptive article itself.

More particularly, the present invention provides an absorptive article having a core material principally consisting of a super water absorbing polymer, said super water absorbing polymer being sandwiched by fluff pulp, characterized in that said fluff pulp is composed of a compressed first site and a further compressed second site, the density of said first site ranging from 0.04 to 0.15 g/cm³, the density of said second site ranging from 0.06 to 0.4 g/cm³, and the area of said second site ranging from 10 to 50% of that of the whole absorptive article.

In other words, the invention also provides a sanitary article which comprises two layers of fluff pulp and a super water absorbing polymer inserted between said layers of fluff pulp, at least one of the fluff pulp layers consisting of a first portion and a second portion in relation to a plane thereof, the first portion having a density of from 0.04 to 0.15 g/cm³, the second portion having a density of from 0.06 to 0.4 g/cm³, the second portion having a larger density than the first portion, the area of the second portion being from 10 to 50 percent of the area of the fluff pulp layer.

The fluff pulp layer to use in the invention article is manufactured by partially compressing fluff pulp so that the first portion and the second portion may be formed as above defined. A pattern of the first portion and the second portion on the fluff pulp layer may be chosen as desired. For example, the first portion is composed of small partitions which are separate from each other and the second portion is composed of continuous stripes which cross each other and surround the first portion.

The use of the super water absorbing polymer as the principal component of the absorptive core material, as mentioned above, means that at least 40% of about 50 cc of urine, i.e. the quantity of urine at one excretion, which was absorbed by the core material, has been absorbed by the super water absorbing polymer after 30 minutes.

An important advantage of the present invention is that the use of a super water absorbing polymer as principal absorptive core material can reduce the amount of fluff pulp and therefore the absorptive material is not hardened even if it is compressed with considerably large pressures. Urine can therefore be effectively diffused by sufficient compression.

Moreover, when such a super water absorbing polymer is used principally, substantial increase in the absorption capacity and decrease in the return of urine cannot be gained unless the super water absorbing polymer is used efficiently. The absorptive core material was compressed for the efficient utilization of this super water absorbing polymer so that urine can be diffused widely into the absorptive core material. Too much compression of the core material, however, results in the hardening of the absorptive material even if the super water absorbing polymer is used principally.

Another important advantage of the present invention concerning this point is that, as the entire absorptive core material is compressed with some pressures and a part of the core material is further compressed with greater pressures, urine is well diffused entirely and further widely diffused in the part where the material is compressed with especially large pressures. Both of the diffusibility of urine and the softness of the absorptive material have thus been achieved. It is necessary for achieving such an appropriate hardening of the material to select the density of the first site of the compressed fluff pulp within the range from 0.04 to 0.15 g/cm³ and that of the further highly compressed second site from 0.06 to 0.4 g/cm³. If the area of the highly compressed second site exceeds 50% of the whole article, the absorptive core material is hardened, while if the area is smaller than 10%, urine cannot be diffused effectively. Accordingly, the area of the second site is preferred to be within the range from 10 to 50%, more preferably from 20 to 40%.

The super water absorbing polymer is sandwiched by fluff pulp in the present invention. The pulp of the upper layer must be 20 to 80% in order to fix the polymer between the upper and the bottom layers of the fluff pulp.

The super water absorbing polymer to be used in the present invention includes starch polymers, acrylate polymers, cellulosic substances and other high-molecular compounds which can absorb water in amounts at least 50 times as much as its own weight, among which polyacrylate compounds such as sodium polyacrylate are most preferable from the viewpoint of absorptivity.

In the practical application of the present invention, the compression of the entire material and that of the part of it may be effected simultaneously or separately. For example, the partial compression may be effected after the entire compression, or the pulp of the upper and the bottom layers may be compressed first and then the super water absorbing polymer together with the pulp sandwiching it compressed partially. Various changes and modifications may be made in the compression of the present invention without departing from the spirit and scope of the invention.

Figure 1:
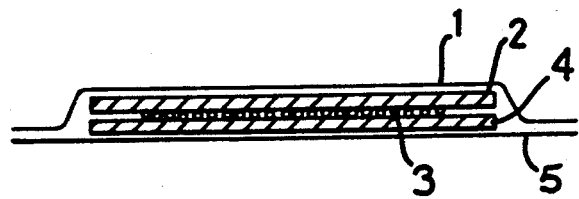
FIG. 1 is a cross section of a disposable diaper as one example of the absorptive article of the present invention.
Figure 2:
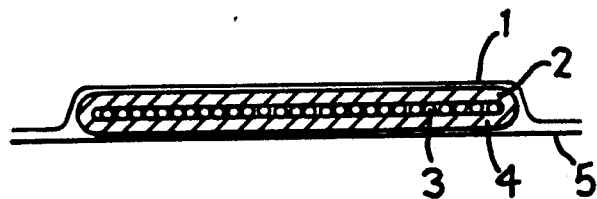
FIG. 2 is a cross section of a disposable diaper as another example.
Figure 3:
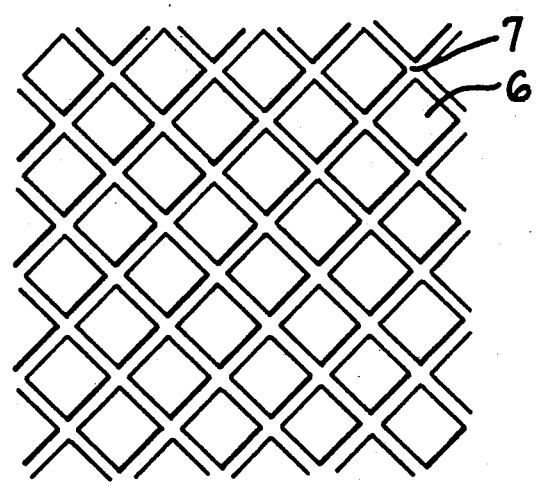
FIG. 3 is a plan view of the absorptive core material of the present invention.
Figure 4:
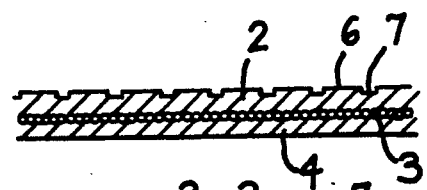
FIGS. 4 to 6 are enlarged cross sections of the absorptive core material of the present invention.
Figure 5:
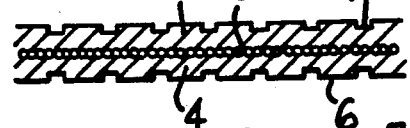
Figure 6:
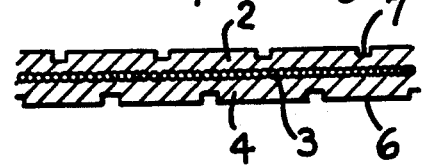

The embodiment of the present invention will now be described in more detail according to the attached drawings The disposable diaper of the present invention as shown in FIGS. 1-6, comprises an absorptive core material in which a super water absorbing polymer 3 is sandwiched by the layers of fluff pulp 2 and 4, said absorptive core material being further covered with a surface sheet 1 and a back surface sheet 5, and the fluff pulp 2 and 4 being composed of a compressed first site 6 and a further compressed second site 7.

The embodiment of the present invention has heretofore been described, but it is our intention that the invention be not limited by this description, and various changes and modifications may be made in the invention without departing from the spirit and scope thereof.

The following is an example of the absorptive article of the present invention.

EXAMPLE 10 g of fluff pulp was divided into approximate halves to form upper and bottom layers, between which 2.5 g of a super water absorbing polymer (sodium polyacrylate) was spread. Then the fluff pulp was compressed as shown in Table 1 to form an absorptive material. 30 ml of artificial urine was allowed to be absorbed by the central part of the prepared absorptive material (120×200 mm). After 15 minutes, the return liquid from 100 cm² of the material at a pressure of 35 g/cm² for 2 minutes was allowed to be absorbed by filter paper and the amount of the return was measured. The touch of the absorptive material was also evaluated. The results are shown in Table 1.

TABLE 1

| density of the first site | density of the second site | proportion of the second site (%) | return amount | touch of the absorptive material | Remarks |
| --- | --- | --- | --- | --- | --- |
| 0.03 | 0.05 | 30 | 10.7 | | comparative examples |
| 0.05 | 0.20 | 60 | 3.2 | X | comparative examples |
| 0.20 | 0.40 | 20 | 1.9 | X | comparative examples |
| 0.10 | 0.60 | 20 | 2.2 | X | comparative examples |
| 0.05 | 0.065 | 5 | 8.8 | | comparative examples |
| 0.065 | 0.20 | 20 | 3.4 | | examples |
| 0.04 | 0.20 | 10 | 4.9 | | examples |
| 0.10 | 0.40 | 30 | 2.8 | Δ | examples |
| 0.065 | 0.10 | 40 | 4.1 | | examples |

The embodiments of the invention in which an exclusive property or privilege is claimed are defined as follows:

1. A sanitary article for absorbing body fluids, comprising a compressed assembly consisting essentially of an upper fluff pulp layer, a lower fluff pulp layer and a core layer of super water-absorbing polymer disposed between and retained by said fluff pulp layers and providing the principal absorbent of the sanitary article, the lateral edges of said core layer being spaced laterally inwardly from the lateral edges of said fluff pulp layers so that the entirety of said core layer is covered by said fluff pulp layers, both of said fluff pulp layers being compressed so as to have an indented lattice pattern on the surfaces thereof remote from said core layer, said surfaces each being comprised of a multitude of compressed small lands which are separated from each other by compressed, criss-crossing, continuous, indented strips wherein each of said lands is surrounded by strips, said lands collectively defining first portions of said fluff pulp layers and having a density of from 0.04 to 0.015 g/cc, said indented strips collectively defining second portions of said fluff pulp layers and having a density higher than the density of said first portions and in the range of from 0.06 to 0.4 g/cc, the areas of said fluff pulp layers that are occupied by said second portions being from 10 to 50 percent of the total areas of said fluff pulp layers.

2. A sanitary article as claimed in claim 1, in which the super water absorbing polymer is sodium polyacrylate.

3. A sanitary article as claimed in claim 1 in which the indented strips on one of said fluff pulp layers are vertically aligned with the indented strips on the other one of said fluff pulp layers.

4. A sanitary article as claimed in claim 1 in which the indented strips on one of said fluff pulp layers are laterally offset from the indented strips on the other one of said fluff pulp layers.

5. A sanitary article as claimed in claim 1 in which the areas of said fluff pulp layers that are occupied by said second portions comprise from 20 to 40 percent of the total areas of said fluff pulp layers.

6. A sanitary article as claimed in claim 2, in which said lands have a density of 0.065 g/cc and said strips have a density of 0.20 g/cc and occupy 20 percent of the total area of said fluff pulp layers.

7. A sanitary article as claimed in claim 2, in which said lands have a density of 0.10 g/cc and said strips have a density of 0.40 g/cc and occupy 30 percent of the total area of said fluff pulp layers.

* * * * *